US009782378B2

(12) United States Patent
Akimoto et al.

(10) Patent No.: US 9,782,378 B2
(45) Date of Patent: Oct. 10, 2017

(54) MICROORGANISMS THAT EXTRACELLULARLY SECRETE LIPID PARTICLES ENCAPSULATING LIPIDS

(75) Inventors: Kengo Akimoto, Osaka (JP); Hiroshi Kawashima, Takatsuki (JP); Sakayu Shimizu, Kyoto (JP)

(73) Assignee: SUNTORY HOLDINGS LIMITED, Osaka-shi, Osaka (JP)

( * ) Notice: Subject to any disclaimer, the term of this patent is extended or adjusted under 35 U.S.C. 154(b) by 1133 days.

(21) Appl. No.: 11/606,983

(22) Filed: Dec. 1, 2006

(65) Prior Publication Data

US 2007/0099279 A1 May 3, 2007

Related U.S. Application Data

(62) Division of application No. 09/807,541, filed as application No. PCT/JP00/05425 on Aug. 11, 2000, now Pat. No. 7,157,254.

(30) Foreign Application Priority Data

Aug. 13, 1999 (JP) .................................... 11-229509

(51) Int. Cl.
| | | |
|---|---|---|
| C12N 1/16 | (2006.01) | |
| A61K 31/202 | (2006.01) | |
| A23C 9/152 | (2006.01) | |
| A23C 11/04 | (2006.01) | |
| A23D 9/00 | (2006.01) | |
| A23L 2/52 | (2006.01) | |
| A61K 8/14 | (2006.01) | |
| A61K 8/92 | (2006.01) | |
| A61K 8/99 | (2017.01) | |
| A61Q 19/00 | (2006.01) | |
| C12P 7/64 | (2006.01) | |
| C12R 1/645 | (2006.01) | |
| A23K 20/158 | (2016.01) | |
| A61K 31/201 | (2006.01) | |
| A23L 31/00 | (2016.01) | |
| A23L 33/12 | (2016.01) | |
| A23L 33/14 | (2016.01) | |

(52) U.S. Cl.
CPC .......... *A61K 31/202* (2013.01); *A23C 9/1528* (2013.01); *A23C 11/04* (2013.01); *A23D 9/00* (2013.01); *A23K 20/158* (2016.05); *A23L 2/52* (2013.01); *A23L 31/00* (2016.08); *A23L 33/12* (2016.08); *A23L 33/14* (2016.08); *A61K 8/14* (2013.01); *A61K 8/92* (2013.01); *A61K 8/925* (2013.01); *A61K 8/99* (2013.01); *A61K 31/201* (2013.01); *A61Q 19/00* (2013.01); *C12P 7/6472* (2013.01); *C12R 1/645* (2013.01); *A23V 2002/00* (2013.01)

(58) Field of Classification Search
CPC .............. C12N 15/8247; C12N 9/1029; A23V 2200/224; A23V 2250/18; A23V 2250/1862; A23V 2250/1868; A23V 2250/187; A61K 31/201; A61K 31/202; A61K 8/92; A61K 8/99; C12P 7/6472; C12R 1/645

USPC ..... 435/320.1, 468, 134, 254.1, 254.11, 171, 435/41, 441, 444; 536/23.2; 800/278, 800/298

IPC ........ C07H 21/04; C07K 14/415; C12N 15/82, 1/16

See application file for complete search history.

(56) References Cited

U.S. PATENT DOCUMENTS

| | | |
|---|---|---|
| 4,885,249 A | 12/1989 | Buxton et al. |
| 5,204,250 A | 4/1993 | Shinmen et al. |
| 5,260,213 A | 11/1993 | Harman et al. |
| 5,322,780 A | 6/1994 | Kawashima et al. |

(Continued)

FOREIGN PATENT DOCUMENTS

| | | |
|---|---|---|
| EP | 0 207 475 | 1/1987 |
| EP | 0 223 960 B1 | 6/1987 |
| EP | 0 276 982 A2 | 8/1988 |

(Continued)

OTHER PUBLICATIONS

Sajbidor, et al., 1990. Arachidonic Acid Production by *Mortierella* sp.S-17. Influence of C/N ratio. Biotechnology Letters, vol. 12, No. 6, pp. 455-456.*

(Continued)

*Primary Examiner* — Debbie K Ware
*Assistant Examiner* — Kailash C Srivastava
(74) *Attorney, Agent, or Firm* — Drinker Biddle & Reath LLP

(57) ABSTRACT

There are provided microorganisms having a property of producing a lipid containing unsaturated fatty acids as constituent fatty acids and extracellularly secreting the produced lipid encapsulated in lipid particles, methods of screening said microorganisms, as well as methods of efficiently producing a fatty acid-containing lipid using said microorganisms. Furthermore, there are provided lipid particles encapsulating a lipid containing unsaturated fatty acids, and foods, cosmetics, and animal feeds comprising said lipid particles added thereto. Artificially treated microorganisms or microorganisms collected from nature are grown on a solid medium, and microbial strains that form lipid particles at the periphery of the colonies and/or microbial strains that, when cultured in a transparent liquid medium, make the culture liquid cloudy are selected. The microorganisms obtained are cultured, lipid-containing lipid particles secreted in the culture liquid, are separated from the culture liquid, and the lipid is separated and purified.

8 Claims, No Drawings

(56) References Cited

U.S. PATENT DOCUMENTS

| | | | |
|---|---|---|---|
| 5,401,646 A | 3/1995 | Shinmen et al. | |
| 7,157,254 B1 * | 1/2007 | Akimoto | A23C 9/1528 435/134 |

FOREIGN PATENT DOCUMENTS

| | | | |
|---|---|---|---|
| EP | 0 535 940 B1 | | 4/1993 |
| EP | 0825263 A2 | | 2/1998 |
| EP | 0972844 A1 | | 1/2000 |
| GB | 2 013 087 | | 8/1979 |
| JP | 62-3791 | | 1/1987 |
| JP | 63-12290 | | 1/1988 |
| JP | 63-14696 | | 1/1988 |
| JP | 63-14697 | | 1/1988 |
| JP | 63-44891 | | 2/1988 |
| JP | 63-240791 | | 10/1988 |
| JP | 5-91887 | | 4/1993 |
| JP | 5-91888 | | 4/1993 |
| JP | 05-91889 | | 4/1993 |
| JP | 06-153970 | | 6/1994 |
| JP | 07-289143 | | 11/1995 |
| JP | 08-089167 | | 4/1996 |
| JP | 08-163990 | | 6/1996 |
| JP | 10-057085 | | 3/1998 |
| WO | WO 94/01001 | | 1/1994 |
| WO | WO-98/39468 | * | 9/1998 |

OTHER PUBLICATIONS

Sajbidor, et al. 1992. Influence of Some Metal Ions on the Lipid Content and Arachidonic Acid Production by *Mortierella* sp. Folia Microbiologica, vol. 37, No. 6, pp. 404-406.*

Nojima et al (1995. Extracellular Formation of Triglycerides from Glucose by a Mutant Strain of Trichosporon. Journal of Fermentation Bioengineering, vol. 80, No. I, pp. 88-90.*

GO: 0005811 Database definition of lipid particle, http://www.ebi.ac.uk/QuickGO/GTerm?id=GO:0005811 Apr. 3, 2011.*

Athenstaedt et al. 1999. Identification and Characterization of Major Lipid Particle Proteins of the Yeast *Saccharomyces cerevisiae*. Journal of Bacteriology, vol. 181, No. 20, pp. 6441-6448.*

Bajpai et al., Arachidonic Acid Production by Fungi.Applied and Environmental Microbiology, vol. 57, pp. 1255-125.*

Certik et al ( 1998. Desaturase-defective fungal mutants: useful tools for the regulation and overproduction of polyunsaturated fatty acids. Trends in Biotechnology (TIBTECH) vol. 16, pp. 500-505.*

Nojima et al (1999. Isolation and characterization of triacylglycerol-secreting mutant strain from yeast, *Saccharomyces cerevisiae*. Journal of General and Applied Microbiology. vol. 45, pp. 1-6.*

Nojima et al., "Extracellular Formation of Triglycerides from Glucose by a Mutant Strain of *Trichosporon*," Journal of Fermentation and Bioengineering, vol. 80, No. 1, pp. 88-90, 1995.

Yagi et al., "Extracellular Production of Palmitoleic Triglycerides by a Yeast, *Trichosporon*," Journal of Fermentation and Bioengineering, vol. 77, No. 2, pp. 164-168.

Office Action issued Jun. 18, 2008, by the European Patent Office in European Application No. 00 951 969.5.

Demain A. et al., "Manual of Industrial Microbiology and Biotechnology," 1986, American Society for Microbiology, p. 188.

Stedman's Medical Dictionary, 1995 (Williams and Wilkins, Baltimore, MD) pp. 121 and 1851.

Sakuzo Fukui, "Selection and Breeding of Microorganisms Secreting and Producing Fuel Lipids," Bio Industry, vol. 12, No. 3 (1995) pp. 36-46 (partial translation).

Osamu Suzuki, "Microbially Produced Fatty Acids and Their Uses," Fragrance Journal, 1989-6, pp. 67-75 (partial translation).

Kamogawa et al., "Preparation of Long-Term Dispersible Oil Droplets Using Fatty Acids and Their Esters," Review of 37th Symposium of Oil Chemists, Sep. 16, 1988, pp. 141 (in Japanses with English Translation).

Nojima et al., "Isolation and characterization of triacylglycerol-secreting mutant strain from yeast, *Saccharomyces cervisiae*," J. Gen. Appl. Microbiol. vol. 45, pp. 1-6 (1999).

Canadian Office Action issued Mar. 28, 2011, in Canadian Application No. 2,347,094.

Kendrick et al., "Lipids of Selected Molds Grown for Production of n-3 and n-6 Polyunsaturated Fatty Acids," Lipids, vol. 27, No. 1, pp. 15-20 (1992).

Sanchez-Muniz et al. 1992. Deep-Frying of Sardines in Different Culinary Fats. Changes in the Fatty Acid Composition of Sardines and Frying Fats. Journal of Agriculture Food Chemistry, vol. 40, pp. 2252-2256.

Ruinen et al. 1964. Composition and properties of the extracellular lipids of *yeast* species from the phyllosphere. Antonie van Leeuwenhoek Journal of Microbiology and Serology, vol. 30, pp. 377-384.

* cited by examiner

MICROORGANISMS THAT EXTRACELLULARLY SECRETE LIPID PARTICLES ENCAPSULATING LIPIDS

This application is a divisional application of U.S. patent application Ser. No. 09/807,541, filed Apr. 13, 2001, now U.S. Pat. No. 7,157,254, which is a National Stage of International Application No. PCT/JP00/05425, filed Aug. 11, 2000, and which claims benefit of Japanese Application No. 11-229509, filed Aug. 13, 1999, all of which are incorporated by reference in their entireties.

Field of the Invention

The present invention relates to microorganisms having a property of extracellularly secreting a lipid containing unsaturated fatty acids encapsulated in small particles, or to microorganism having a property of extracellularly secreting a lipid containing unsaturated fatty acids that have 18 carbons and three or more double bonds or 20 or more carbons and two or more double bonds, and more specifically to microorganisms having a property of extracellularly secreting a lipid containing unsaturated fatty acids encapsulated in small particles, said microorganisms being obtained by artificially treating microorganisms that have an ability of producing and intracellularly accumulating a lipid containing unsaturated fatty acids, or to microorganisms having a property of extracellularly secreting a lipid containing unsaturated fatty acids that have 18 carbons and three or more double bonds or 20 or more carbons and two or more double bonds, said microorganisms being obtained by artificially manipulating microorganisms that have an ability of producing and intracellularly accumulating a lipid containing unsaturated fatty acids that have 18 carbons and three or more double bonds or 20 or more carbons and two or more double bonds, and to methods of efficiently producing a lipid containing unsaturated fatty acids using said microorganisms, as well as to methods of screening said microorganisms, and furthermore to lipid particles encapsulating a lipid that contains unsaturated fatty acid, and to foods, cosmetics, and animal feeds comprising said lipid particles added thereto.

Background Art

In recent years, various biological activities of highly unsaturated fatty acids have attracted attention. For example, arachidonic acid is considered to be a precursor of prostaglandins, thromboxanes, prostacyclins, leucotrienes and the like that have biological activities such as uterine contraction and relaxation, vasodilation, and hypotensive activity. These substances have been under intensive research, together with docosahexaenoic acid, in recent years, as elements essential for the development of babies and infants. Various foods, cosmetics, and animal feeds to which a lipid containing highly unsaturated fatty acids such as γ-linolenic acid, dihomo-γ-linolenic acid, and eicosapentaenoic acid in addition to arachidonic acid and docosahexaenoic acid have been added are also attracting attention, and some of the products to which highly unsaturated fatty acids has been added are commercially available.

Accordingly, methods of efficiently producing these highly unsaturated fatty acids also are being studied intensively.

For example, methods of efficiently producing arachidonic acid, dihomo-γ-linolenic acid, γ-linolenic acid, or eicosapentaenoic acid by fermentation have been developed using microorganisms belonging to, for example, the genus Mortierella, specifically the subgenus Mortierella, that are known to produce highly unsaturated fatty acids such as arachidonic acid, dihomo-γ-linolenic acid, γ-linolenic acid, and eicosapentaenoic acid (Japanese Unexamined Patent Publication (Kokai) No. 63-44891, Japanese Unexamined Patent Publication (Kokai) No. 63-12290, Japanese Unexamined Patent Publication (Kokai) No. 63-14696, Japanese Unexamined Patent Publication. No 5-91887, and Japanese Unexamined Patent Publication (Kokai) No. 63-14697). There is also known a method of producing mead acid using a mutant strain in which Δ12 desaturation activity is decreased or missing, said strain being obtained by effecting mutation to microorganisms belonging to genus Mortierella subgenus Mortierella (Japanese Unexamined Patent Publication (Kokai) No. 5-91888).

Thus, the production of a lipid containing highly unsaturated fatty acids using microorganisms that produce said fatty acids is increasingly becoming a major source of highly unsaturated fatty acids. These microorganisms have a property of not only using highly unsaturated fatty acids they produce as constituents of the cell membrane but also accumulating highly unsaturated fatty acids as fat and oil (triglycerides) containing them as constituent fatty acids in the cell. By utilizing the fats and lipids accumulated in the cell, high productivity of highly unsaturated fatty acids have come to be secured.

In this conventional production method, the amount of fat and oil obtained per culture was a product of the cell mass of the microorganism obtained by culturing and the amount of fat and oil produced per cell, and thereby how to increase the cell mass and the amount of fat and oil per cell was a challenge to be solved in order to attain enhanced production of fat and oil. Research has so far revealed that the selection of culture conditions permits increases in both of the above to a certain extent, but there are certain limits to each of them with increases in the cell mass being limited by physical factors such as the volume of the culture tank and increases in the amount of fat and oil per cell being limited by physiological factors of the microorganism used.

On the other hand, when it is desired to utilize a lipid produced by and accumulated in the cell of the microorganism, it is necessary to collect the cells after culturing, process the cells with a mill etc., to disrupt the cell membrane, and then to extract the lipid accumulated in the cell.

If substances produced by a microorganism could be secreted outside of the cell instead of being accumulated in the cell, the physiological burdens placed on the microorganism by the substances produced can be alleviated and thus the microorganism can continue to produce the products; in the isolation and extraction of microbial products as well, extraction from the culture only is needed, which provides an advantage that treatment becomes simplified and microorganisms can be continuously processed as they remain alive.

Based on the above, efforts to extracellularly secret a lipid accumulated in the cell have recently been made by Sakuzo Fukui at al. (BIG INDUSTRY 12: 36-46 (1995)) . Sakuzo Fukui et al. conducted research on the production and secretion of lipids by microorganisms to develop novel biological fuel that can replace fossil fuel, and have successfully bred genus Trichosporon yeast to convert sugar and n-alkanes to lipids and to secret them outside of the cell. They further demonstrated that the constituent fatty acid species of extracellularly secreted triglyceride (TG) are oleic acid, palmitic acid, linoleic acid, and stearic acid. However, it has a drawback that the TG that is directly secreted outside of the cell is incorporated into the cell again and metabolized.

However, microorganisms that have an ability to produce lipids containing unsaturated fatty acids that have 18 carbons and three or more double bonds or 20 or more carbons and two or more double bonds, and that have a property of extracellularly secreting the produced lipid, or microorganisms that have an ability of producing an unsaturated fatty acid-containing lipid, and that secrete the produced lipid encapsulated in small particles instead of directly secreting them at the time of extracellular secretion thereof, are not known.

In a study on γ-linolenic acid production by molds described in "Microbially produced fatty acids and their uses", Osamu Suzuki, Fragrance Journal 1989 (6), pp. 67-75, it is reported that a surfactant was added to a culture medium of a microorganism of the genus *Mucor* to allow the leakage of some of lipids outside of the cell. However, it relates to methods of artificially destroying the cell membrane to allow lipids accumulated in the cell to leak out of the cell, and does not utilize the ability of the cell per se to extracellularly secrete lipids produced in the cell.

Thus, there is a need to find microorganisms that have an ability of producing a lipid containing unsaturated fatty acids that have 18 carbons and three or more double bonds or 20 or more carbons and two or more double bonds, and have a property of extracellularly secreting the produced lipids, or microorganism that have an ability of producing an unsaturated fatty acid-containing lipid, and that have a property of extracellularly secreting the produced lipids encapsulated in small particles, and to develop methods of efficiently producing lipids that contain unsaturated fatty acids using said microorganisms.

Incidentally, in order to find microorganisms that have novel abilities, the development of an efficient screening method for microorganisms having such abilities is a prerequisite. In the above breeding of genus *Trichosporon* yeast that converts sugar and n-alkanes into lipids and extracellularly secrete them, the following screening method was adopted. Thus, yeast colonies that appeared on an agar plate medium (YPD medium etc.) are UV-treated (15 watts at a distance of 30 cm for 15 minutes) (this treatment is intended to suppress the dispersion of colony cells during layering treatment and not to induce mutation), the UV-treated colony plates are layered with a YPD soft agar medium containing $10^5$ cells of a test strains, and are then cultured at 28° C. for 2 days. As the test strains, the A-1 strain and the ole-1 strain having auxotrophy for saturated fatty acids and unsaturated fatty acids, respectively, are used and those colonies giving a larger halo (the micro colony ring of the test strain) around them are selected as lipid-secreting strains. The selection of lipid-secreting strains employs two media: a soft agar medium containing or not containing lipase.

This method has a major drawback that although it can be applied to screening of yeast for which layering is possible, it cannot be applied to screening of microorganisms for which layering is impossible. There is additional disadvantage that the assay method are complicated.

Thus, in order to find microorganisms that have an ability of producing a lipid containing unsaturated fatty acids that have 18 carbons and three or more double bonds or 20 or more carbons and two or more double bonds, said microorganisms having a property of extracellularly secreting the produced lipids, there is a need for the development of a screening method that permits simple and efficient screening of said microorganisms and that can be applied to various microorganisms, and the development of a new screening method for finding microorganisms that can secrete the produced lipids encapsulated in small particles at the time of extracellular secretion of the produced lipids.

Disclosure of the Invention

Thus, the present invention intends to provide microorganisms that have an ability of producing a lipid containing unsaturated fatty acids that have 18 carbon and three or more double bonds or 20 or more carbons and two or more double bonds, and have a property of extracellularly secreting the produced lipids, or said microorganisms that have an ability of producing unsaturated fatty acids, secrete the produced lipids encapsulated in small particles, and methods of efficiently producing said lipids using said microorganisms, as well as methods of screening said microorganisms. The present invention also intends to provide lipid particles encapsulating a lipid containing unsaturated fatty acids, and to foods, cosmetics, and animal feeds comprising said lipid particles added thereto.

After intensive research to attain the above objectives, the inventors of the present invention have found that by artificially treating microorganisms that have an ability of producing and intracellularly accumulating a lipid containing unsaturated fatty acids, it is possible to create microorganisms that have an ability of extracellularly secreting the produced lipids encapsulated in small particles.

In order to obtain microorganisms having the desired ability from the group of artificially treated microorganisms or microorganisms collected from nature, the following simple screening method has been found that could be easily practiced by a person skilled in the art. Thus, as a primary screening, artificially treated strains or strains collected from nature are grown on solid media, and thereby those strains providing lipid particles around the colonies are selected. Then as a secondary screening, the strains selected in the primary screening are cultured under shaking in a transparent liquid medium (4% glucose, 1% yeast extract, pH 6.0) at 28° C. for 2 days. Microorganisms that accumulate lipids in the cell do not make the medium cloudy during culturing, whereas microorganisms that extracellularly secrete the produced lipids make the medium cloudy, and therefore, microorganisms having an ability of extracellularly secreting lipids can be easily screened by a mere visual confirmation of the degree of cloudiness of the culture liquid.

Then, it was found that, the efficient extracellular secretion of the lipid particles encapsulating said lipids utilizing the microorganisms obtained may be effected by culturing the microorganisms in a medium having enhanced glucose concentration and/or enhanced pH.

It was also found that the extracellularly secreted lipid particles can be easily separated from the culture liquid by centrifugation and that centrifugation and chromatography in addition to extraction with common organic solvents can be used to isolate lipids in the lipid particles.

Furthermore, the inventors have found that since the lipid particles encapsulating the lipids separated from the culture liquid have a property of being easily dispersed in water or hydrophilic substances and stably retain the lipids against oxidation, the lipid particles may be added as they are to foods, cosmetics, or animal feeds thereby to obtain foods, cosmetics, or animal feeds containing unsaturated fatty acids that have novel features, and have completed the present invention.

Embodiment for Carrying Out the Invention

According to the present invention, unsaturated fatty acids that have 18 carbons and three or more double bonds, or 20 or more carbons and two or more double bonds refer to, for example, 5,8,11,14-eicosatetraenoic acid (arachidonic acid), 8,11,14-eicosatrienoic acid. (dihomo-γ-linolenic acid), 6,9,12-octadecatrienoic acid (γ-linolenic acid), 5,8,11,14,17-eicosapentaenoic acid, 8,11,14,17-eicosatetraenoic acid, 6,9,12,15-octadecatetraenoic acid (stearidonic acid), 9,12,15-octadecatrienoic acid (α-linolenic acid), 4,7,10,13, 16,19-docosahexaenoic acid (DHA), 8,11-eicosadienoic acid, 5,8,11-eicosatrienoic acid (Mead acid), 7,10,13,16-docosatetraenoic acid, 4,7,10,13,16-docosapentaenoic acid, 7,10,13,16,19-docosapentaenoic acid, and the like.

The present invention provides microorganisms that have a property of extracellular secreting a lipid containing unsaturated fatty acids that have 18 carbons and three or more double bonds or 20 or more carbons and two or more double bonds, or microorganisms that have a property of extracellularly secreting a lipid containing unsaturated fatty acids encapsulated in small particles. More specifically, the present invention provides microorganisms that can extracellularly secret a intracellularly produced lipid directly or by encapsulating it in small particles, said microorganisms being obtained by artifitially treating microorganisms that have an ability of producing and intracellularly accumulating a lipid containing unsaturated fatty acids that have 18 carbons and three or more double bonds or 20 or more carbons and two or more double bonds, or that have an ability of producing and intracellularly accumulating a lipid containing unsaturated fatty acids.

As used herein, microorganisms that have an ability of producing and intracellularly accumulating a lipid containing unsaturated fatty acids include, for example, conventionally known microorganisms that have an ability of producing γ-linolenic acid or microorganisms that have an ability of producing arachidonic acid, microorganisms that have an ability of producing DHA, microorganism that have an ability of producing ω9 highly unsaturated fatty acids, and the like. Microorganisms that have an ability of producing arachidonic acid include microorganisms belonging to genus *Mortierella*, genus *Conidiobolus*, genus *Pythium*, genus *Phytophthora*, genus *Penicillium*, genus *Cladosporium*, genus *Mucor*, genus *Fusarium*, genus *Aspergillus*, genus *Rhodotorula*, genus *Entomophthora*, genus *Echinosporangium* and genus *Saprolegnia*. As microorganisms belonging to genus *Mortierella* subgenus *Mortierella*, there can be mentioned *Mortierella elongata*, *Mortierella exigua*, *Mortierella hydrophila*, *Mortierella alpina*, *Mortierella schmuckeri*, *Mortierella minutissima*, and the like. Specifically there can be mentioned strains *Mortierella elongata* IFO8570, *Mortierella exigua* IFO8571, *Mortierella hygrophila* IFO5941, *Mortierella alpina* IFO8568, ATCC16266, ATCC32221, ATCC42430, CBS219.35, CBS224.37, CBS250.53, CBS343.66, CBS527.72, CBS529.72, CBS608.70, and CBS754.68, and the like.

These strains are all available without limitations from the Institute of Fermentation (IFO) in Osaka, Japan, and American Type Culture Collection (ATCC) in the U.S.A., and Centrralbureau voor Schimmelcultures (CBS). It is also possible to use *Mortierlla elongata* SAM0219 (FERM P-8703) (FERM BP-1239), a microbial strain isolated from the soil by the present inventor. Microbial strains belonging to these type cultures or those isolated from nature may be used as they are, and spontaneous mutants obtained by effecting growth and/or isolation once or more may be used wherein the mutants have different properties than that of the original strains.

In accordance with the present invention, as microorganisms having the above ability of producing unsaturated fatty acids, there can be used the microorganisms in which at least one of the Δ5 desaturation reaction, the Δ6 desaturation reaction, the Δ9 desaturation reaction, the Δ12 desaturation reaction, the ω3 desaturation reaction, and chain elongation reaction is enhanced, or reduced or missing may be obtained by for example, mutation treatment or gene manipulation described below.

As artificial treatment effecting the above microorganisms, there can be mentioned mutation, gene manipulation, cell fusion and the like. Mutation according to the present invention can be conducted by conventional mutation treatments: for example effecting irradiation treatment (X ray, gamma ray, neutron beams), ultra violet irradiation, and high temperature treatment to induce mutation; and by suspending microorganisms in a suitable buffer etc., to which a mutagen is added followed by incubating for a given time, which is diluted appropriately and inoculated on an agar medium to obtain colonies of mutant strains.

As mutagens, there can be mentioned alkylating agents such as nitrogen mustard, methyl methane sulfonate (MMS), and N-methyl-N'-nitro-N-nitrosoquanidine (NTG), base analogs such as 5-bromouracil, antibiotics such as mitomycin C, base synthesis inhibitors such as 6-mercaptopurine, dyes such as proflavine, certain carcinogens such as 4-nitroquinoline-N-oxide, and other compounds such as manganese chloride and formaldehyde. Microorganisms used may be live cells (mycelia) or spores.

In gene manipulation, conventional gene recombinant technology is used.

From microorganism groups subjected to the above artificial treatment or microorganism groups collected from nature according to conventional methods, strains of interest may be isolated based on the following method. As a primary screening, after strains subjected to artificial treatment or strains collected from nature are plated on a solid medium, the presence of lipid particles around colonies are used as an index to select strains, and then as a secondary screening, the strains selected in the primary screening are evaluated in a liquid medium as to whether they secrete a lipid outside of the cell. In an evaluation method, for example, 4 ml of a transparent liquid medium (4% glucose, 1% yeast extract, pH 6.0) is dispensed in a test tube, which is sterilized at 120° C. for 20 minutes, and then one platinum loopful of the strain that was selected in the primary screening is inoculated and incubated under shaking at 28° C. for 2 days.

Microorganisms like those belonging to genus *Mortierella* subgenus *Mortierella* that produce triglyceride having an unsaturated fatty acid as constituent fatty acids in the cell but do not secrete it outside of the cell, even when cultured in the above liquid medium, do not make the medium cloudy, but when the lipid produced is secreted outside of the cell the medium becomes cloudy, so that the microorganisms that extracellularly secrete the lipid can be easily confirmed. When the cloudness does not change after being allowed to stand for some time, a lipid has been secreted as lipid particles, whereas when the lipid has been directly secreted, a lipid layer rises up to the surface of the medium, so that the two can be easily discriminated from each other. As components of the medium used in the secondary screening, any liquid medium that can become transparent may be selected as appropriate, and any composition or the medium may be selected that is suitable for the growth of the microorganism to be evaluated.

From among the strains selected in this manner, it is preferred to select strains that have an ability to grow and to produce lipids equal to or better than the that of the parent strain used for artifcial treatment. Although microorganisms of interest may be selected from either one of the above primary screening or the above secondary screening depending on the microorganism to be selected or the purpose of the study, combination of the two can assure better selection. When the above two screening methods are combined, either the primary screening or the secondary screening may be conducted first.

As a strain obtained by the above method, there can be used *Mortierella alpina* SAM2241 (FERM BP-7272) or SAM 2242 that was derived from *Mortierella alpina* IFO 8568 by the present inventors and that extracellularly secretes an intracellularly produced lipid encapsulated in small particles, but the strain to be used is not limited, and strains that extracellularly secrete the lipid intracellularly produced may be readily obtained by the above screening method, all of which can be used.

Microorganisms of the present invention obtained by the above screening method are microorganisms that can be converted to spheroplast or protoplast, and microorganisms of the present invention can be used to obtain protoplast in which the cell wall has been completely removed or spheroplast in which part of the cell wall remains. This property cannot be observed in the parent strain used for artificial treatment such as mutation treatment, and is probably due to the fact that the mutation treatment changed the structure of the cell wall and made it fragile.

A microbial strain obtained as described above that, for example, strains that extracellularly secretes an intracellularly produced lipid encapsulated in small particles in the following method may be used to obtain lipid particles or the lipid. In order to culture microorganisms of the present invention, the spores, the mycelia, or the preculture obtained by culturing in advance are inoculated into a liquid medium and cultured.

In the case of liquid media, the carbon sources used include, but are not limited to, any of glucose, fructose, xylose, saccharose, maltose, soluble starch, molasses, glycerol, mannitol and the like that are commonly used. As nitrogen sources, in addition to natural nitrogen sources such as peptone, yeast extract, malt extract, meat extract, casamino acid, corn steep liquor, soybean protein, defatted soybean, and cottonseed meal, organic nitrogen sources such as urea, and inorganic nitrogen sources such as sodium nitrate, ammonium nitrate, and ammonium sulfate can be used.

When desired, inorganic salts such as phosphates, magnesium sulfate, iron sulfate, and copper sulfate, and vitamins can also be used as trace nutrients. The concentrations of these medium components are not limited as long as they do not adversely affect microbial growth. Generally from the practical viewpoint, carbon sources are in the range of 0.1 to 40% by weight and preferably 1 to 25% by weight. Furthermore, the sequential addition of carbon sources and/or increasing initial concentrations of carbon sources can promote extracellular secretion of lipids. Nitrogen sources may be in the range of 0.1 to 10% by weight and preferably 0.1 to 6% by weight, and the nitrogen sources may be fed in the middle of culturing.

Though the optimum growth temperature as used herein may vary depending on the microorganism used, it is 5 to 40° C., preferably 20 to 30° C., or after culturing at 20 to 30° C. to grow the cell mass, culturing at 5 to 20° C. may be continued to produce a lipid containing unsaturated fatty acids. By means of such temperature control, the amount of highly unsaturated fatty acids in the produced fatty acids can be enhanced. pH of the medium is 4 to 10, preferably 5 to 9, and aerated agitation culture, shaking culture, or continuous or stationary culture may be conducted using bioreactors. By using the initial pH of 5 to 9, preferably 6 to 9, and more preferably 7 to 9, extracellular secretion of lipids can be promoted. Culturing is usually conducted for 2 to 30 days, preferably 5 to 20 days, and more preferably 5 to 15 days.

In accordance with the present invention, by adding precursors of the desired unsaturated fatty acids to the medium and then culturing, the production of the desired unsaturated fatty acids, for example 5,8,11,14-eicosatetraenoic acid (arachidonic acid), 8,11,14-eicosatrienoic acid (dihomo-γ-linolenic acid), 6,9,12-octadecatrienoic acid (γ-linolenic acid), 5,8,11,14,17-eicosapentaenoic acid, 8,11,14,17-eicosatetraenoic acid, 6,9,12,15-octadecatetraenoic acid (stearidonic acid), 9,12,15-octadecatrienoic acid (α-linolenic acid), 4,7,10,13,16,19-docosahexaenoic acid (DHA), 8,11-eicosadienoic acid, and 5,8,11-eicosatrienoic acid (Mead acid) can be promoted.

Precursors that may be used include, but not limited to, hydrocarbons such as tetradecane, hexadecane, and octadecane, fatty acids such as tetradecanoic acid, hexadecanoic acid, and octadecanoic acid or salts (e.g., sodium. salts and potassium salts) or esters thereof, or fat and oil containing fatty acids (e.g. olive oil, coconut oil, calm oil, flaxseed oil, fish oil, and microbial oil) as constituent ingredients.

By adding fat and oil containing, as constituent ingredients unsaturated fatty acids (for example, fish and microbial oil), or said unsaturated fatty acids to the medium and culturing, the microorganisms of the present invention incorporate the added unsaturated fatty acids or fat and oil into the cell and extracellularly secrete the lipid containing said unsaturated fatty acids as lipid particles. Therefore, even if unsaturated fatty acids that are not originally produced by the microorganism are used, it is possible to produce lipid particles encapsulating the lipid containing such unsaturated fatty acids as constituent fatty acids.

The total amount of the added substrate containing the above precursor is 0.001 to 10% by weight and preferably 0.5 to 10% by weight relative to the medium. These substrates may be added either before or immediately after inoculating the production microorganism, or after the start of culturing, or they may be added at both time points. The addition after the start of culturing may be once or more than once on an intermittent basis. Alternatively, they may be added continuously. Alternatively, these substrates may be used as the sole carbon source for culturing.

By culturing the microorganisms of the present invention as described above, a lipid containing unsaturated fatty acids can be produced and accumulated in large quantities in the cell, and said lipid is secreted directly or as lipid particles encapsulated in small particles. When a liquid medium is used, lipid particles or the lipid can be harvested from the culture or the cultured liquid from which cultured cells have been removed as in the following manner.

After culturing is over, cultured cells are separated from the culture using conventional means for separating solids and liquids such as centrifugation and filtration to obtain a medium (referred to as culture liquid) in which lipid particles encapsulating lipids are dispersed. From the culture liquid, lipid particles encapsulating lipids may be isolated as one containing medium components by lyophilization, or lipid particles containing no medium components may only be isolated by conventional centrifugation or column treatment. For example, a centrifuge (TOMYRL-101) or a swing rotor (TS-7) may be used for centrifugation at a maximum centrifugal force of 1000× g or greater, preferably 1500× g or greater for about 10 minutes to separate lipid particles.

The lipid particles obtained in the above methods are composed of sugars, proteins, and lipids Their composition excluding water comprises 0 to 70%, preferably 20 to 60%, of sugars, 0 to 40%, preferably 10 to 30%, of proteins, and 20 to 100%, preferably 30 to 80%, of lipids. However, the ratio of sugars, proteins, and lipids may vary depending on the culture condition, and is not limited to the above ratio. In fact, water is included. in some cases.

The lipid particles of the present invention have an average diameter of 0.2 to 10 μm, preferably 2 to 4 μm with the diameter of the largest lipid particle being 40 μm, preferably 10 μm. They can be separated by centrifugation; for example, a centrifuge (TOMYRL-101) or a swing rotor (TS-7) may be used. for centrifugation at a maximum centrifugal force of 1000× g or greater, preferably 1500× g or greater, for about 10 minutes to separate lipid particles. Furthermore, the lipid particles of the present invention may be easily dispersed in water or hydrophilic substances, and they have a property of stably retaining lipids against oxidation.

Harvesting of a lipid in the lipid particles can be carried out either directly from the culture liquid before separating the lipid particles or from the lipid particles separated from the culture liquid. When it is extracted from the lipid particles separated from the culture liquid, it is extracted in a manner similar to that conventionally performed to extract lipids from the cells. Thus, lipid particles are extracted with an organic solvent under a stream of nitrogen. As organic solvents, ether, hexane, methanol, ethanol, chloroform, dichloromethane, petroleum ether and the like can be used, and satisfactory results can also be obtained by alternate extraction with methanol and petroleum ether, or by extraction with a single layer solvent of chloroform-methanol-water. When they are directly extracted from the culture liquid before separation of the lipid particles, similar organic solvents may be used, however, in practice the use of a solvent that can be separated from water is preferred, and considering their application to foods, the use of hexane is preferred. Evaporation of organic solvents from the extract under reduced pressure yields a lipid containing unsaturated fatty acids.

In the lipids obtained as above, unsaturated fatty acids are present in the form bound to triglyceride, phosphatidylcholine, phosphatidylethanolamine, phosphatidylinositol and the like. The lipids are composed of glycerides (triglycerides, diglycerides, monoglycerides), phospholipids, fatty acids, glycolipids, sterol esters and the like, and glycerides in the lipid are 50 to 100%, preferably 70 to 100%, phospholipids are 0-50%, preferably 0 to 30%, fatty acids, glycolipids, and sterol esters combined are 0 to 30%, preferably 0 to 15%. Triglycerides in the lipids are 50 to 100%, preferably 70 to 100%.

The lipid composition in a lipid containing unsaturated fatty acids produced using the microorganisms of the present invention derived from microorganisms belonging to genus *Mortierella* is 70 to 100% by weight of neutral lipids, 0 to 30% by weight of polar lipids, and triglyceride, a main component of the neutral lipids, is 70 to 99% by weight in the lipids. The contents of unsaturated fatty acids may vary depending on the microorganisms and culture conditions used, and the content of arachidonic acid relative to the total fatty acids is not smaller than 10% by weight, preferably 20 to 100% by weight, and more preferably 40 to 100% by weight. The ratio of arachidonic acid to the total fatty acids in triglycerides is not smaller than. 10% by weight, preferably 15 to 100% by weight, and more preferably 35 to 90% by weight. However, the present invention is not limited to lipid particles secreted by microorganisms belonging to subgenus *Mortierella*, and fatty acids produced are not limited to arachidonic acid, either. Furthermore, after allowing the cell to incorporate the lipid added to the culture medium, they may be allowed to be secreted as lipids in lipid particles, and thereby the lipid composition of lipids in lipid particles and the ratio of fatty acids of interest are varied, and in a sense can be freely designed.

In order to isolate and purify triglycerides containing unsaturated fatty acids from an unsaturated fatty acid-containing lipid collected from the lipid particles or the culture liquid, standard methods are used such as deoxygenation, degumming, dehydration, steam distillation, molecular distillation, cooling separation, and column chromatography.

In order to separate unsaturated fatty acids from a containing unsaturated fatty acids, they are used in the form of mixed fatty acids or mixed fatty acid esters and concentrated and separated by conventional methods such as urea addition, cooling separation, and column chromatography.

The lipid particles of the present invention contain, in abundance, unsaturated fatty acids in the form of triglycerides. Their applications include, but not limited to, raw materials of foods, beverages, cosmetics, pharmaceuticals, animal feeds and the like and additives thereof. Besides, their objective of uses and the amount used are not limited in any way.

For example, foods include, in addition to general foods, functional foods, nutrient supplements, formula for premature infants, formula for babies, baby foods, foods for pregnant women or foods for the aged people. The lipid particles of the present invention have excellent dispersion properties to water or hydrophilic substances, and therefore they can be added to foods containing no fat and oil the addition to which having conventionally been impossible, in particular various beverages. Furthermore, since the lipid particles of the present invention can stably retain lipids against air oxidation, the addition to foods containing conventional fat and oil can be effected more easily. As foods containing fat and oil, there can be mentioned, for example, natural foods originally containing fat and oil such as meat, fish, or nuts, foods such as soup to which fat and oil are added during cooking, processed foods that uses fat and oil as heat medium such as doughnuts, fat and oil foods such as butter, processed foods to which fat and oil are added during processing such as cookies, or foods to which fat and oil are sprayed or pasted during processing finishing such as hard biscuits. Furthermore, they may be in the form of functional foods and pharmaceuticals, and for example they may be in the processed form such as enteric nutrients, powders, granules, troches, medicines, suspensions, emulsions, syrups, and drinks.

EXAMPLES

The present invention will now be explained in more details with reference to specific examples. It should be noted, however, that the present invention will not limited by these examples in anyway.

Example 1

Obtaining a Microbial Strain That Extracellularly Secretes Lipid Particles by Mutation of *Mortierella alpina* IFO8568

*Mortierella alpina* IFO8568 was inoculated into a large slant bottle containing 300 ml of Czapek agar medium (0.2% $NaNO_3$, 0.1% $K_2HPO_4$, 0.05% $MgSO_4·7H_2O$, 0.05% KCl, 0.01% $FeSO_4·7H_2O$, 3% sucrose, 2% agar, pH 6.0), and was cultured at 28° C. for 2 weeks.

After culturing, 50 ml of sterile water to which had been added 2 drops of Tween 80 was added to the large slant bottle, which was shaken sufficiently, and then filtered with 4 ply gauze. This procedure was repeated twice, and the filtrate was centrifuged at 8000× g for 10 minutes. Spores thus obtained were suspended. into 50 mM Tris/maleate buffer solution (pH 7.5) to 1×10⁶/ml to prepare a spore solution.

To 1.0 ml of the spore solution thus obtained, 0.5 ml of 100 mM Tris/maleate buffer solution (pH 7.5) was added, and 500 µl of the NTG solution (5 mg of N-methyl-N'-nitro-N-nitrosoguanidine per ml of deionized water) was added, which was subjected to mutation treatment by incubating at 28° C. for 15 minutes. After adding 3 ml of 10% $Na_2S_2O_3$, the reaction mixture was centrifuged at 5500× g for 10 minutes, and the precipitate (spores subjected to mutation treatment) was washed with 3 ml of sterile water and centrifuged at 5500× g for 10 minutes, to which sterile water was added to prepare a NTG-treated spore suspension.

The NTG-treated spore suspension was diluted to about $10^{-3}$ to $10^{-4}$ and then plated on a GY agar plate (1% glucose, 0.5% yeast extract, 0.005% Triton X-100, 1.5% agar, pH 6.0). After incubating at 28° C., those that developed colonies were examined for morphology with a result that microbial strains having a growth morphology distinctly different from that of the parent strain were obtained. The entire colonies of the highly unsaturated fatty acid-producing microbial strains including the parent strain were covered with mycelia as the strain accumulate the produced lipids in the cell, whereas the mutants obtained were covered with lipid particles.

Subsequently, 4 ml of a transparent liquid medium (4% glucose, 1% yeast extract, pH 6.0) was dispensed into a test tube and sterilized at 120° C. for 20 minutes. Then a platinum loopful of the microbial strain obtained above was inoculated thereinto and cultured under shaking at 28° C. for 2 days, which made the medium cloudy. Even after allowing the medium to stand for over 10 minutes, no lipid layers were observed on the surface of the medium. Thus, the lipid was possibly secreted as lipid particles.

The lipid particles that covered the colonies obtained in the culturing on the GY agar plate were analyzed for lipid by thin layer chromatography (TLC). To a previously activated plate (Merck 5554, 200×200×0.25 mm, silica gel 60F-254, aluminium sheet), the sample and the control (phospholipids, triglycerides, fatty acids) were plated, which was developed with n-hexane:diethylether:acetic acid=80:20:2 (V/V/V) using phosphomolybdic acid (10% phosphomolybdic acid in ethanol) and primulin (0.01% primulin in 80% acetone) as a color developer. For primulin, bands were examined under UV light of a long wavelength (366 nm). As a result, the majority of the lipids in the lipid particles observed outside of the cell were found to be triglycerides.

Thus, about 3000 colonies yielded mutants *Mortierella alpina* SAM2241 FERM BP-7272 and SAM2242 that extracellularly secrete lipid particles encapsulating mainly triglycerides having highly unsaturated fatty acids as constituent fatty acids.

Example 2

Fatty Acid Analysis of an Extracellularly Secreted Lipid When *Mortierella alpina* SAM2241 That Extracellularly Secretes Lipid Particles was Cultured on Various Media Four ml each of medium A, B, C, D, E, and F was distributed in a test tube, and was sterilized at 120° C. for 20 minutes. A platinum loopful of *Mortierella alpina* SAM2241 (FERM BP-7272) obtained in Example 1 was inoculated into the medium, and cultured under shaking at 28° C. for 2 days and then at 12° C. for 7 days. After culturing, the cells and the filtrate were separated by filtration. The filtrate obtained was placed in a screw-capped test tube (16.5 mmφ), and lyophilized. To this were added 1 ml of methylene chloride and 2 ml of anhydrous methanol-hydrochloric acid (10%), which was methylesterified by treating at 50° C. for 3 hours. Four ml of n-hexane and 1 ml of water were added to this, and then extracted twice. The solvent after extraction was evaporated using a centrifuge evaporator (40° C., 1 hour), and the fatty acid methylesters thus obtained were analyzed by capillary gas chromatography. At the time of adding the methylester, 0.2 mg/ml n-heptadecanoic acid (17:0) was added as an internal standard, and fatty acids were quantitated based on the ratio of surface area of GLC.

| Medium A | Glucose | 1.0% |
|---|---|---|
| | $K_2HPO_4$ | 0.3 |
| | $MgSO_4 \cdot 7H_2O$ | 0.02 |
| | Polypeptone | 1.5 |
| | NaCl | 0.2 |
| | Yeast extract | 0.1 |
| | pH 7.0 | |
| Medium B | Polypeptone | 1.0% |
| | Meat extract | 0.5 |
| | Yeast extract | 0.1 |
| | NaCl | 0.5 |
| | pH 7.0 | |
| Medium C | Glucose | 5.0% |
| | Polypeptone | 0.5 |
| | $KH_2PO_4$ | 0.2 |
| | $K_2HPO_4$ | 0.1 |
| | $MgSO_4 \cdot 7H_2O$ | 0.02 |
| | Yeast extract | 0.1 |
| | pH 6.5 | |
| Medium D | Glucose | 2.0% |
| | Yeast extract | 1.0 |
| | Bactopeptone | 1.0 |
| Medium E (MRS medium) | Glucose | 2.0% |
| | Meat extract | 1.0 |
| | Yeast extract | 0.5 |
| | Casein trypsin digest | 1.0 |
| | $K_2HPO_4$ | 0.2 |
| | Sodium acetate | 0.5 |
| | Diammonium citrate | 0.2 |
| | $MgSO_4 \cdot 7H_2O$ | 0.02 |
| | $MnSO_4 \cdot 7H_2O$ | 0.02 |
| | Tween 80 | 0.1 |
| Medium F | Glucose | 1.0% |
| | Yeast extract | 0.5 |
| | pH 6.5 | |

The result is shown in Table 1.

TABLE 1

The composition of extracellularly secreted fatty acids in the lipid obtained on various media

| | 16:0 | 18:0 | 18:1 (n − 9) | 18:2 (n − 6) | 18:3 (n − 6) | DGLA | AA | Others |
|---|---|---|---|---|---|---|---|---|
| Medium A | 14 | 8 | 20 | 11 | 4 | 4 | 31 | 8 |
| Medium B | 15 | 6 | 28 | 16 | 9 | — | 26 | — |

TABLE 1-continued

The composition of extracellularly secreted fatty acids in the lipid obtained on various media

|  | 16:0 | 18:0 | 18:1 (n − 9) | 18:2 (n − 6) | 18:3 (n − 6) | DGLA | AA | Others |
|---|---|---|---|---|---|---|---|---|
| Medium C | 17 | 14 | 13 | 10 | 3 | 2 | 37 | 4 |
| Medium D | 14 | 9 | 23 | 9 | 5 | 2 | 31 | 7 |
| Medium E | 16 | 3 | 30 | 11 | 7 | 2 | 27 | 4 |
| Medium F | 15 | 5 | 23 | 10 | 5 | 3 | 32 | 7 |

16:0, palmitic acid;
18:0, stearic acid;
18:1 (n − 9), oleic acid;
18:2 (n − 6), linoleic acid;
18:3 (n − 6), γ-linoleic acid;
DGLA, dihomo-γ-linoleic acid;
AA, arachidonic acid In any of the media, a lipid containing unsaturated fatty acids were observed to be extracellularly secreted. Furthermore, the total amount of the extracellularly secreted lipid obtained for medium A to F and the amount of arachidonic acid were found to be positively correlated with glucose concentration. Thus, the total amount of lipid per test tube was 0.18 and 0.6 mg at a glucose concentration of 1%, 0.53 and 0.96 mg at a glucose concentration of 2%, and 2.11 mg at a glucose concentration of 5%, and the amount of arachidonic acid per test tube was 0.05 and 0.15 mg at a glucose concentration of 1%, 0.11 and 0.19 mg at a glucose concentration of 2%, and 0.62 mg at a glucose concentration of 5%.

A result with similar tendency was obtained for the mutant SAM2242.

Example 3

The Amount of Arachidonic Acid Produced by Aerated Agitating Culture Using a 10 L Jar Fermentor of Mortierella alpina SAM2241 that Extracellularly Secretes Lipid Particles Five liters of a medium (A: pH 5.0, B: pH 6.0, C: pH 7.0) containing 2% glucose, 1.5% soy flour, 0.3% $KH_2PO_4$, 0.1% $Na_2SO_4$, 0.05% $MgCl_2 \cdot 6H_2O$, 0.05% $CaCl_2 \cdot 2H_2O$, and 0.2% soybean oil was placed in a 10 L jar fermentor, and sterilized at 120° C. for 30 minutes. Mortierella alpina SAM2241 (FERM BP-7272) obtained in Example 1 was inoculated therein, and were subjected to aerated agitating culture at an aeration rate of 1.0 vvm and a culture temperature of 24° C. for 10 days, 2.0% glucose was added on day 1 of culturing, 1.5% glucose on day 2, 1.0% glucose on days 3 and 4, and 0.5% glucose on days 5 and 6.

Sampling was carried out every day. The culture liquid was separated by filtration. into the cells and the filtrate (extracellularly secreted lipid particles are dispersed therein). The cells were dried at 105° C. for 2 hours, and 20 mg of the dried cells was placed in a screw-capped test tube (16.5 mmφ)and was subjected to methylesterification as in Example 2. The filtrate (1 ml) was placed in a screw-capped test tube (16.5 mmφ), was lyophilized, and then was subjected to methylesterification as in Example 2. The fatty acid esters thus obtained were analyzed by capillary gas chromatography. Table 2 shows the amount produced of arachidonic acid and its content on day 9 of culturing.

TABLE 2

The amount produced of arachidonic acid and its content on day 9 of culturing

|  | In the cell | Outside of the cell | Extracellular arachidonic acid percentage (%) |
|---|---|---|---|
| Medium A pH 5.0 | 6.4 g/L(33.2%) | 0.14 g/L(37.4%) | 2.1 |
| Medium B pH 6.0 | 5.8 g/L(32.4%) | 0.24 g/L(34.5%) | 4.0 |
| Medium C pH 7.0 | 3.6 g/L(29.7%) | 0.43 g/L(30.8%) | 10.7 |

Figures in parentheses indicate the ratio of arachidonic acid relative to the total fatty acids.

With increased pH of the medium, the extracellular secretion of arachidonic acid-containing lipids was prompted.

Example 4

Lipid Analysis of Lipid Particles Secreted by Mortierella alpina SAM2241 That Extracellularly Secretes Lipid Particles The culture filtrates on day 9 of culturing in medium A, B, and C obtained in Example 3 were treated with. chloroform/methanol/water (1:2:0.8) by the Blight-Dyer method and the total lipids were extracted from the extracellularly secreted lipid particles. The total lipids obtained contained neutral lipids (triglycerides) and polar lipids (phospholipids). The total extracted lipids were charged into the Sep-pak Silica cartridge (manufactured by Waters) and eluted to obtain the neutral lipid fraction with chloroform and the polar lipid fraction with methanol. After evaporating the solvent, methylesterification was carried out as in Example 2, and fatty acid methylesters obtained were analyzed by capillary one chromatography. As a percentage of the total fatty acids to which triglycerides and phospholipids bind, the percentages of triglyceride and phospholipids were calculated. As a result, the percentage of the triglycerides in the total lipids for medium A, B, and C were 95.3%, 97.7%, and 96.2%, respectively.

Example 5

Continuous Culture of Mortierella alpina SAM2241 That Extracellularly Secrets Lipid Particles in a 10 L Bioreactor To a 10 L bioreactor having two built-in ceramic filters, 5 L of a medium containing 2% glucose and 2% yeast extract with pH adjusted to 7 was prepared, to which a precultured microbial strain of *Mortierella alpina* SAM2241 (FERM BP-7272) obtained in Example 1 was inoculated and subjected to aerated agitating culture. On the next day, a glucose solution was added through a ceramic filter to increase the glucose concentration in the medium by 3%. On day 2 also, the glucose solution was added through the ceramic filter to increase the glucose concentration in the medium by 3%.

On day 3 and after, a 5% glucose solution and a 0.05% yeast extract solution were continuously passed through a ceramic filter at a speed of about 1000 ml/day. And the culture liquid was continuously extracted through a ceramic filter at about 600 ml/day (the amount of is adjusted to remain constant). In order to prevent the clogging of the filter with the cells, feeding of the glucose and yeast extract solutions and extracting of the culture liquid were alternately carried out as appropriate. Due to evaporation of water vapor by aeration, the amount of liquid in the jar remained almost constant. The feeding speed of glucose was adjusted by the glucose concentration to he extracted.

As a result, a medium (culture liquid) that contained about 1 g/L arachidonic acid-containing triglycerides was able to be continuously extracted.

Example 6

Microbial Transformation of the Fat and Oil Added to the Medium and its Migration into Lipid Particles by *Mortierella alpina* SAM2241 That Extracellularly Secretes Lipid To 2 ml of a medium (pH 6.0) containing 1% glucose and 1% yeast extract, 2% linseed oil or fish oil was added, which was then put into a 10 ml Erlenmeyer flask and sterilized at 120° C. for 20 minutes. One platinum loopful of *Mortierella alpina* SAM2241 (FERM BP-7272) obtained in Example 1 was inoculated into the medium, and cultured using a reciprocating shaker (150 rpm) at 28° C. for 8 days. The filtrate was recovered by filtration, was lyophilized, and then the extracellularly secreted lipid was subjected to methyl-esterification as in Example 2, and the fatty acid methylester was analyzed by capillary gas chromatography.

When linseed oil was added to the medium, a major fatty acid of linseed oil, 9,12,15-octadecatrienoic acid (α-linolenic acid) served as a substrate of the fatty acid biosynthetic enzymes of the mutant, and was converted to 6,9,12,15-octadecatetraenoic acid (stearidonic acid), 8,11,14,17-eicosatetraenoic acid, and 5,8,11,14,17-eicosapentaenoic acid, and the lipid in the lipid particles contained 2.4, 3.3, and 8.1% of 6,9,12,15-octadecatetraenoic acid (stearic acid), 8,11,14,17-eicosatetraenoic acid and 5,8,11,14,17-eicosapentaenoic acid, respectively, confirming that the converted fatty acids are extracellularly secreted as the constituent fatty acids of triglycerides. When fish oil was added to the medium, the fact that 5,8,11,14,17-eicosapentaenoic acid and 4,7,10,13,16,19-docosahexaenoic acid of fish oil are incorporated into the microbial strain and are extracellularly secreted as constituent fatty acids of triglycerides was confirmed because the lipid of the extracellularly secreted lipid particles contained 8.1 and 12.2% of 5,8,11,14,17-eicosapentaenoic acid and 4,7,10,13,16,19-docosahexaenoic acid, respectively.

Example 7

Component Analysis of Lipid Particles Extracellularly Secreted by *Mortierella alpina* SAM2241

In order to analyze components of extracellularly secreted lipid particles, a spore suspension of *Mortierella alpina* SAM2241 obtained in Example 1 was plated to the Gtr agar plate (1% glucose, 0.5% yeast extract, 0.005% Triton X-100, 1.5% agar, pH 6.0), and cultured at 28° C. for 4 days. As shown in Example 1, the entire colonies were covered with lipid particles. Thus, the small particles were collected into a screw-capped test tube (16.5 mmφ). Chloroform (2 ml) and KCl solution (2 ml) were added thereto, shaken and extracted. Lipids migrated into the chloroform layer and sugars and proteins migrated into the KCl layer, and these were analyzed for the components according to a standard method and were found to comprise sugars: 38.1%, proteins: 18.2%, lipids: 43.7%.

Example 8

Preparation of Formula Using Lipid Particles

The culture filtrate obtained in Example 3 was separated using a centrifuge (TOMY RL-101) at 1500× g and washed with sterile water to prepare lipid particles fit for consumption. The lipid particles (0.92 g) were added to 100 g of powdered milk to prepare a formula containing lipid particles. The composition of arachidonic acid in the formula obtained way 0.5% of the total fatty acids, which was similar to that of the mother's milk.

When the formula was dissolved in water, its dispersion in water was good and uniformly dispersed without any separation of oils.

Example 9

Preparation of Capsules

Water was added to 100 parts per weight of gelatin and 35 parts per weight of food additive glycerin, which was dissolved at 50 to 60° C. to prepare a gelatin coating with a viscosity of 20000 cps. Then, from the lipid particles separated by centrifugation from the culture filtrate obtained in Example 3, lipids were extracted and purified according to a standard method. Then, 97% the refinded oil and 3% vitamin E oil were mixed to prepare a content. Using these, capsule molding and drying were carried out according to a standard method so that soft capsules containing 180 mg content per capsule were produced.

Example 10

Preparation of Lipid Particles-Containing Beverages

The lipid particles (10 g) fit for consumption obtained in the method shown in Example 8 were added to 10 L of orange juice to prepare juice containing lipid particles.

Reference to the microorganisms deposited under the Patent Cooperation Treaty, Rule 13-2, and the name of the Depository Authority Depository Authority:
Name: the National Institute of Bioscience and Human Technology, Agency of Industrial Science and Technology
Address: 1-3, Higashi 1-chome, Tsukuba city, Ibaraki Pref., Japan Organism (1)
  Name: *Mortierella elongata* SAM0219
  Accession number: FERM BP-1239
  Date deposited: Mar. 19, 1986

Organism (2)
  Name: *Mortierella alpina* SAM2241
  Accession number: FERM BP-7272
  Date deposited: Aug. 11, 2000

The invention claimed is:

1. A composition comprising isolated lipid particles extracellularly secreted by a mutated *Mortierella alpina*, wherein the isolated lipid particles encapsulate an unsaturated fatty acid-containing lipid, wherein the isolated lipid particles comprise 20-60% sugar, 0-30% protein, and 30-80% lipid, wherein the mutated *M. alpina* grows into colonies covered with the lipid particles on a solid medium, or produces a cloudy culture liquid in a transparent liquid medium, and wherein the isolated lipid particles are produced by *M. alpina* SAM 2241 or *M. alpina* SAM 2242.

2. The composition of claim 1, wherein the unsaturated fatty acid-containing lipid contains an unsaturated fatty acid having 18 or more carbons and two or more double bonds.

3. The composition of claim 1, wherein the microorganism is cultured in a liquid medium, and wherein the isolated lipid particles are obtained from a culture liquid.

4. The composition of claim 1, wherein the isolated lipid particles can be uniformly dispersed in water or a hydrophilic substance.

5. The composition of claim 1, wherein the isolated lipid particles stably retain the unsaturated fatty acid-containing lipid thereby preventing oxidation of the unsaturated fatty acid.

6. The composition of claim 1, wherein the isolated lipid particles are isolated by centrifugation and/or filtration.

7. The composition of claim 1, wherein the isolated lipid particles have an average diameter of 0.2 to 10 μm.

8. The composition of claim 1, wherein the unsaturated fatty acid-containing lipid comprises 50% or more triglyceride.

* * * * *